(12) United States Patent
Han et al.

(10) Patent No.: US 7,575,914 B2
(45) Date of Patent: Aug. 18, 2009

(54) MICROORGANISM PRODUCING HYALURONIC ACID AND PURIFICATION METHOD OF HYALURONIC ACID

(75) Inventors: Hee-Yong Han, Seongnam (KR); Seung-Hong Jang, Daejeon (KR); Eul-Chae Kim, Yongin (KR); Jung-Kyung Park, Daejeon (KR); Young-Jin Han, Daejeon (KR); Chung Lee, Yongin (KR); Heung-Soon Park, Seoul (KR); Yun-Cheul Kim, Suwon (KR); Ho-Jin Park, Seongnam (KR)

(73) Assignees: Kolon Life Science, Inc., Kwacheon (KR); Vacctech Corp., Daejeon (KR)

( * ) Notice: Subject to any disclaimer, the term of this patent is extended or adjusted under 35 U.S.C. 154(b) by 405 days.

(21) Appl. No.: 10/523,769

(22) PCT Filed: Aug. 19, 2003

(86) PCT No.: PCT/KR03/01666

§ 371 (c)(1),
(2), (4) Date: Oct. 5, 2005

(87) PCT Pub. No.: WO2004/016771

PCT Pub. Date: Feb. 26, 2004

(65) Prior Publication Data

US 2006/0127987 A1    Jun. 15, 2006

(30) Foreign Application Priority Data

Aug. 19, 2002 (KR) .................. 10-2002-0048915
Aug. 19, 2002 (KR) .................. 10-2002-0048916

(51) Int. Cl.
*C12N 1/20* (2006.01)

(52) U.S. Cl. ................................. 435/253.4; 435/885

(58) Field of Classification Search .............. None
See application file for complete search history.

(56) References Cited

U.S. PATENT DOCUMENTS

| | | | |
|---|---|---|---|
| 4,517,295 A | 5/1985 | Bracke et al. | |
| 4,780,414 A | 10/1988 | Nimrod et al. | |
| 4,784,990 A | 11/1988 | Nimrod et al. | |
| 5,023,175 A | 6/1991 | Hosoya et al. | |

FOREIGN PATENT DOCUMENTS

| | | |
|---|---|---|
| CA | 2225866 | 6/1999 |
| CN | 1099068 | 2/1995 |
| CN | 1195027 | 10/1998 |
| DE | 19548954 | 7/1997 |
| JP | 58-56692 A | 4/1983 |
| JP | 62-257382 A | 11/1987 |
| JP | 63-12293 A | 1/1988 |
| JP | 2-103203 A | 4/1990 |
| JP | 6-199656 A | 7/1994 |
| JP | 6-319580 A | 11/1994 |
| JP | 8-23992 A | 1/1996 |
| JP | 9-143078 A | 6/1997 |
| JP | 11-60608 A | 3/1999 |
| JP | 2000-189185 A | 7/2000 |
| JP | 2000-189186 A | 7/2000 |
| JP | 2001-131503 A | 5/2001 |
| KR | 1994-0002478 A | 2/1994 |
| KR | 1994-0024058 A | 11/1994 |
| KR | 1997-0042603 A | 7/1997 |
| KR | 0149793 | 6/1998 |
| WO | WO 95/33067 | 12/1995 |

*Primary Examiner*—David M. Naff
*Assistant Examiner*—Deborah K. Ware
(74) *Attorney, Agent, or Firm*—Birch, Stewart, Kolasch & Birch, LLP

(57) ABSTRACT

The present invention relates to a hyaluronic acid producing strain *Streptococcus* sp. KL0188 and a method for purifying hyaluronic acid, more particularly to a *Streptococcus* sp. KL0188 that does not express hyaluronidase and is non-hemolytic, and a method for purifying hyaluronic acid using an aromatic adsorption resin and an active carbon.

1 Claim, No Drawings

MICROORGANISM PRODUCING HYALURONIC ACID AND PURIFICATION METHOD OF HYALURONIC ACID

BACKGROUND OF THE INVENTION (a) Field of the Invention

The present invention relates to a hyaluronic acid producing microorganism strain and a method for purifying hyaluronic acid, and particularly to Streptococcus sp. KL0188 and a method for purifying hyaluronic acid using an aromatic adsorption resin and an active carbon.

(b) Description of the Related Art

Hyaluronic acid, which is a colorless highly viscous polysaccharide having a molecular weight of 50,000 to 13,000,000 Da, has repeat units of glucuronic acid and N-acetyl glucosamine that are alternately bonded as (1-3) and (1-4). Hyaluronic acid has a moisturizing effect, an excellent lubricating effect against physical friction, and it offers excellent protection effects against invasion of bacteria, etc. Hyaluronic acid is widely used as a cosmetic additive, a treating agent for arthritis, a supplementary agent for ophthalmic operations, an adhesion inhibitor after surgical operations, etc. A lot of hyaluronic acid is contained in cow eyeballs, cock combs, buffer tissue of animals, placentas, cancer cells, skin, etc.

Hyaluronic acid can be extracted from the above-mentioned bio-tissues (U.S. Pat. No. 4,141,973 and U.S. Pat. No. 4,303,676), or it can be collected as a fermentation product by fermenting microorganisms. However, hyaluronic acid obtained by extraction contains impurities such as chondroitin sulfate, glycosamino glycansulfate, etc. hence a complicated purification process is required in order to remove these impurities causing a high production cost. However, according to the production method of hyaluronic acid using microorganisms, production cost is comparatively low, and high molecular weight hyaluronic acid can be obtained by a relatively simple method (Japanese Patent Laid-Open publication No. 58-056692, U.S. Patent 86-00066).

Microorganisms used for the production of hyaluronic acid include Streptococcus pyogenes, Streptococcus faecalis, Streptococcus dysgalactiae, Streptococcus zooepidemicus, Streptococcus equi, Streptococcus equisimilis, etc. According to Bergy's manual, these pertain to Lancefield's serological group A or C. Such microorganisms are hemolytic Streptococcus, and they are reported to have beta-hemolytic functions.

Since hyaluronic acids that are produced using Streptococcus sp. microorganisms (Japanese Patent Laid-Open Publication No. 58-566922, U.S. Patent Laid-Open Publication No. 60-500997, Korean Patent Registration Publication No. 10-250573, and Korean Patent Laid-Open Publication No. 10-250573) have relatively low average molecular weights of 300,000 to 3,500,000 Da, it is difficult to use them as a medicinal treating agent or supplementary agent, and they have insufficient moisturizing power for cosmetics. In addition, U.S. Pat. No. 6,090,596 describes a method for producing high molecular weight hyaluronic acid with molecular weight of 6,300,000 to 9,500,000 Da, but productivity of hyaluronic acid is 0.35 g per L of culture solution, which is very low.

Known methods for separating and purifying hyaluronic acid using microorganisms are as follows:

U.S. Pat. No. 4,157,296 discloses a method for purifying hyaluronic acid by treating a culture solution of Streptococcus pyogenes with trichloro acetic acid to remove strains, and then precipitating it using an organic solvent. However, since the precipitation method using an organic solvent requires numerous repetitive operations, it has a comparatively high cost and consumes substantial time.

U.S. Pat. No. 4,782,046 describes a purification process of introducing 0.01% anionic surfactant of lauryl sulfate into a culture solution of Streptococcus equi to separate hyaluronic acid attached to cell walls, and then introducing a non-ionic surfactant of hexadecyltrimethyl ammonium bromide to form a hyaluronic acid precipitate, and precipitating it with alcohol.

U.S. Pat. No. 4,784,990 describes a purification process of adding ethanol to a culture solution of Streptococcus zooepidemicus to separate hyaluronic acid from microorganisms, and then precipitating it with cetyl pyridinium chloride.

Japanese Patent Laid-Open Publication No. 63-012293 describes a method for removing both low molecular weight hyaluronic acid with a molecular weight of 1,500,000 Da or less and exothermic material by treating a hyaluronic acid-containing solution with a macroreticular anion exchange resin (Dianion HPA-25, HPA-75, IRA-900, IRA-904).

Japanese Patent Laid-Open Publication No. 13-131503 describes a method for purifying hyaluronic acid by treating a hyaluronic acid-containing solution with alumina or silica gel, etc. to remove exothermic material, proteins, nucleic acid, metal impurities, etc., and precipitating it with an organic solvent.

Japanese Patent Laid-Open Publication No. 06-199656 describes a method for purifying hyaluronic acid by passing a hyaluronic acid-containing solution through a membrane filter charged on a solution of pH 6 to 10 to remove exothermic material, and precipitating it with alcohol.

Korean Patent Laid-Open Publication No. 1994-2478 describes a method for purifying hyaluronic acid by adding iron aluminate powders to a hyaluronic acid producing strain culture solution.

In addition, Korean Patent Laid-Open Publication No. 1997-42603 describes a method for purifying hyaluronic acid by treating a hyaluronic acid-containing solution with a hydrophobic polymer (polyethylene, polypropylene, or polystyrene), and then adding active alumina, and precipitating it with alcohol.

However, the above-mentioned methods involve complicated treating processes, which increase production cost, and it is difficult to completely remove exothermic material, proteins, nucleic acid, etc.

SUMMARY OF THE INVENTION

It is an object of the present invention to provide a microorganism strain that can produce high molecular weight hyaluronic acid with a high yield.

It is another object of the present invention to provide a hyaluronic acid producing microorganism strain that does not express hyaluronidase and is not hemolytic.

It is another object of the present invention to provide a high molecular weight hyaluronic acid that is produced from a non-hemolytic microorganism strain and purified.

It is another object of the present invention to provide a method for purifying hyaluronic acid produced from microorganisms, which can remove exothermic material in an easy and straightforward manner, and separate hyaluronic acid with high purity.

In order to achieve these objects, the present invention provides Streptococcus sp. KL0188 (KCTC1024BP), which does not express hyaluronidase and is non-hemolytic.

The present invention also provides a method for purifying hyaluronic acid and a salt thereof, by treating a culture solution of a hyaluronic acid producing microorganism strain with an aromatic adsorption resin, treating it with an active carbon, and precipitating it with an organic solvent.

DETAILED DESCRIPTION OF THE PREFERRED EMBODIMENTS

The present invention relates to a hyaluronic acid producing microorganism strain and a purification method of hyaluronic acid.

According to the present invention, Streptococcus sp. KL0188 that is prepared by causing mutation in Streptococcus zooepidemicus is provided. The Streptococcus sp. KL0188 has been deposited with the Korean Collection for Type Culture (KCTC), on May 10, 2002, under Accession No. KCTC 10248BP. The KCTC is located in Korea Research Institute of Biosience and Biotechnology (KRIBB), 52 Oundong, Yusong-Ku, Taejon 305-333, Republic of Korea. The Streptococcus sp. KL0188 is a non-hemolytie strain, and it can produce hyaluronic acid with a high yield because it does not have hyaluronidase activity.

The Streptococcus sp. KL0188 can be cultured on a culture medium containing trace elements such as a carbon source, a nitrogen source, inorganic salts, vitamins, etc. As the carbon source, glucose, sucrose, galactose, or fructose can be used, and preferably glucose is used. As the nitrogen source, ammonium nitrate, ammonium sulfate, tryptone, peptone, yeast extract, or casamino acid can be used; and as the inorganic salt, sodium chloride, sodium phosphate, disodium phosphate, ferrous sulfate, or magnesium sulfate can be used.

The example of the culture medium for Streptococcus sp. KL0188 that is used in the present invention comprises: 20 to 80 g/L of glucose, 5 g/L of yeast extract, 17 g/L of casein peptone, 7 g/L of glutamic acid, 0.7 g/L of magnesium sulfate, 2.5 g/L of potassium phosphate, and 5.0 g/L of sodium chloride.

The Streptococcus sp. KL0188 can be cultured at 30 to 37° C. under aerobic conditions. The pH of the culture solution is preferably maintained within the range of 6.5 to 7.5, and as the pH changes during culture it is preferably controlled by artificial means. The pH can be controlled using a 5N NaOH solution or 1N HCl solution. If the pH goes beyond the above range, production and molecular weight of hyaluronic acid may be varied.

Hyaluronic acid produced from Streptococcus sp. KL0188 can be separated and purified by common methods (J. Soc. Cosmet. Japan. 22, 35-42 (1988)) or by the purification method of the present invention. The Streptococcus sp. KL0188 produces approximately 6.0 to 7.5 g/L of hyaluronic acid, with a high average molecular weight of 4,000,000 Da or more.

Therefore, according to the present invention, the Streptococcus sp. KL0188 can produce hyaluronic acid with a low cost and high yield, and hyaluronic acid can also be purified by a relatively simple method. In addition, the hyaluronic acid produced therefrom can be used for cosmetics or a medicinal treating agent or supplementary agent.

The purification method of the present invention, which differs from the existing hyaluronic acid precipitation method using surfactants, comprises the steps of active carbon treatment, aromatic adsorption resin treatment, ultra-filtration, and ethanol precipitation of a hyaluronic acid producing microorganism strain culture solution.

As the aromatic adsorption resin, a styrene divinyl benzo-type resin from Mitsubishi Company can be used. Specifically, it is selected from the group consisting of HP10, HP20 (styrene and divinylbenzene copolymer), HP21, HP30, SP800, SP825, SP850, SP875, SP205, SP206, and SP207 (brominated polystyrene), and preferably HP20 or SP207 is used.

As the hyaluronic acid producing strain, any strain that produces hyaluronic acid as a metabolite can be used, and representatively, Streptococcus sp. microorganisms can be used. The Streptococcus sp. microorganisms include Streptococcus pyogenes, Streptococcus faecalis, Streptococcus dysgalactiae, Streptococcus zooepidemicus, Streptococcus equi, Streptococcus equisimilis, and Streptococcus sp. KL0188 (KCTC10248BP). The hyaluronic acid producing strains can be cultured by a common culture method to prepare a culture solution comprising hyaluronic acid.

More specifically, the purification method of hyaluronic acid comprises the steps of (a) preparing a culture filtrate from a culture solution of a hyaluronic acid producing strain; (b) adding an aromatic adsorption resin to the culture filtrate, agitating, and conducting ultrafiltration to prepare a hyaluronic acid solution; and (c) adding an organic solvent to the hyaluronic acid aqueous solution to precipitate hyaluronic acid or a salt thereof, and drying it. The method further comprises the step of adding active carbon to the culture filtrate or to the hyaluronic acid aqueous solution and agitating it, and then removing the active carbon, after the step (a) or (b).

In the step (a), lauryl sulfate and formalin are added to the culture solution and they are agitated, thereby separating hyaluronic acid from the bacteria surface and simultaneously deactivating the bacteria. Then, the culture solution is centrifuged to separate a supernatant, or it is filtered to obtain a filtrate.

The step (b) is conducted after titrating the culture filtrate to a pH of 7.5 to 8.5, and the aromatic adsorption resin is added in an amount of 0.1 to 10 wt %. After adding the aromatic adsorption resin, the mixed filtrate is agitated at 4 to 10° C. so that endotoxins are adsorbed, and it is then filtered to obtain a filtrate from which the adsorption resin is removed. Ultrafiltration of the filtrate is conducted to remove various culture medium ingredients and inorganic salts. The ultrafiltration can be conducted using a filtration membrane with a molecular cut-off of 10,000 to 100,000 Da.

In the step (c), hyaluronic acid or a salt thereof is precipitated by a common organic solvent precipitation method. As the organic solvent, an aqueous organic solvent such as acetone, methanol, ethanol, propanol, isopropanol, or acetonitrile can be used, and preferably ethanol is used. NaCl is added to a hyaluronic acid aqueous solution to the concentration of 0.5 to 3M, the solution is filtered, and an organic solvent is added to the filtrate in a volume of 1 to 5 times that of the filtrate to precipitate hyaluronic acid and its salt. The precipitate is then washed with 70% ethanol and dried.

The active carbon treatment can be conducted after the step (a) or (c). Specifically, to the culture filtrate of the step (a) or to the hyaluronic acid of the step (b), 0.1 to 3 (w/v) % of NaCl is added, and then 0.1 to 10 (w/v) % of active carbon is added. The active carbon is used to adsorb proteins or nucleic acid to remove it.

The purification method of hyaluronic acid can efficiently remove exothermic material, proteins, nucleic acid, and metal impurities, compared to the conventional method, and can minimize organic solvent precipitation frequency and hence prepare hyaluronic acid with a high purity by a simple and economical purification process. Accordingly, hyaluronic acid purified by the purification method of the present invention has a high purity of 99% and thus it can be used for cosmetics or medicines.

The present invention will be described with reference to the following examples. However, these are only to illustrate the present invention and the present invention is not limited to them.

EXAMPLE 1

Screening of Mutant Strain

Mutation was caused on *Streptococcus zooepidemicus* to select mutant strains that have non-hemolytic properties and do not have hyaluronidase activities.

*Streptococcus zooepidemicus* (KCTC 3318) was inoculated on 50 ml of Baco Todd Hewitt Broth from DIFCO Company and cultured at 37° C. until an algebraic growth period occurred. Then, 1 ml of the culture solution was centrifuged at a low temperature to recover precipitated cells, and 50 mM of tris-maleic acid buffer solution (pH 6.0) was added thereto and washed twice.

The cells were dispersed in a buffer solution at a concentration of $1 \times 10^3$ cells/ml, and NTG (N-methyl-N'-nitrosoguanidine) was mixed therewith at a concentration of 200 μg/ml. The mixture was agitated at 37° C. for 30 minutes, and then the cells were washed with 50 mM of tris-maleic acid buffer solution (pH 6.0) twice. The cells were inoculated on Todd Hewitt Broth and cultured at 37° C. for 18 hours. The culture solution was obtained and then diluted with sterile saline solution to a concentration of $1 \times 10^3$ cells/ml, and 0.1 ml of the diluted solution was cultured on Blood Agar to select colonies that did not show hemolysis.

On the selected non-hemolytic mutant strains, mutation was caused by the same method as mentioned above to select strains that do not have hyaluronidase activity. The non-hemolytic mutant strains were coated on a Todd Hewitt Agar Broth containing 400 μg of hyaluronic acid and 1% albumin fraction V so that a single colony could be formed. Standing culture was conducted in a wet chamber at 37° C. for 2 to 5 days, and then 10 ml of 2N acetate solution was added and stood for 10 minutes. Colonies that showed rapid growth and largely form viscous material were selected.

The selected colonies were respectively inoculated on 1.5 L of culture medium for hyaluronic acid production, and aerobically cultured at 35° C., pH 6.95 to 7.05, for 20 hours. The culture solution was recovered and absolute viscosity was measured at 25° C. using a digital viscometer (Brookfield DVII+, 4 spin, 30 rpm). A part of the solution was precipitated with an organic solvent, dissolved in distilled water, and hyaluronic acid production was quantified by the carbazole method (Z. Dische, J. Biol. Chem. 167, 189 (1949)), thereby selecting strains that have high absolute viscosity of culture solution and show high hyaluronic acid production.

The selected strains were identified by analyzing the amino acid sequence of 16S rDNA (Jukes, T. H. & C. R., (1969). In mammalian protein metabolism, pp. 21-132; Edited by H. N. Munro., Saito, N. & Nei, M. (1987) Mol Biol vol 4, 406-425). As a result, the selected strains were identified as *Streptococcus* sp. hence they were named *Streptococcus* sp. KL0188. The *Streptococcus* sp. KL0188 was deposited with the Korean Collection for Type Culture on May 10, 2002, under deposition No. KCTC 10248BP.

EXAMPLE 2

Inspection of Hyaluronic Acid Productivity

*Streptococcus* sp. KL0188 was cultured to measure hyaluronic acid production efficiency and the molecular weight of produced hyaluronic acid.

The separated microorganisms were inoculated on 100 ml of Todd Hewitt Broth and cultured at 35° C. until an algebraic growth period occurred, and then used as a first seed culture solution. The first seed culture solution was inoculated on 1 L of tryptic soy broth (Difco, USA) and cultured at 35° C. until an algebraic growth period occurred, and then used as a second seed culture solution.

In a 30 L fermenter, a hyaluronic acid production culture medium containing 60 g/L of glucose, 5 g/L of yeast extract, 17 g/L of casein peptone, 7 g/L of glutamic acid, 0.7 g/L of magnesium sulfate, 2.5 g/L of dipotassium phosphate, and 5.0 g/L of sodium chloride was introduced and sterilized, and 1000 ml of the second seed culture solution was inoculated therein. Aerobic culture was conducted while maintaining the pH of the culture solution within the range of 6.95 to 7.05, a temperature of 35° C., and a ventilation amount of 1.0 VVM.

During culture, some amount of the sample was taken and viscosity of the culture solution was measured, and culture was conducted until the viscosity no longer increased. It was determined through measuring that the viscosity of the culture solution did not increase after being cultured for 20 hours, and thus the culture was stopped. Maximum viscosity was approximately 20,000 cps.

Hyaluronic acid existing in the culture solution was recovered by a known separation and purification method (J. Soc. Cosmet. Japan. 22, 35-42 (1988)). Hyaluronic acid was quantified by a carbazole method (Z. Dische, J. Biol. Chem. 167, 189 (1947)), and the average molecular weight of the produced hyaluronic acid was measured by a capillary viscometer method (Narlin, Analytical Biochemistry 147, 347-395 (1985)). As a result, hyaluronic acid production amount was confirmed as 7.0 g/L and the average molecular weight was 5,500,000 Da.

COMPARATIVE EXAMPLE 1

Examination of Hyaluronic Acid Productivity of *Streptococcus zooepidemicus*

*Streptococcus zooepidemicus* (KCTC3318) was cultured by the same method as in Example 2, and hyaluronic acid productivity and molecular weight were measured.

After 24 hours, viscosity of the culture solution did not increase and thus culture was stopped. The viscosity was measured to be approximately 4000 cps, hyaluronic acid productivity was 3.0 g/L, and average molecular weight was 2,500,000 Da.

It was confirmed that the *Streptococcus* sp. KL0188 of the present invention has excellent hyaluronic acid productivity and the molecular weight of the produced hyaluronic acid was high, compared to *Streptococcus zooepidemicus*.

The *Streptococcus* sp. KL0188 of the present invention is a non-hemolytic strain, and produces hyaluronic acid with a high molecular weight and a high yield. Therefore, hyaluronic acid produced from the

*Streptococcus* sp. KL0188 can be used for cosmetics or medicines.

EXAMPLE 3

Purification of Hyaluronic Acid Using Aromatic Adsorption Resin SP207

3-1. Preparation of Hyaluronic Acid Producing Strain

*Streptococcus* sp. KL0188 (KCTC10248BP) was inoculated on 100 ml of Todd Hewitt Broth and cultured at 35° C. until an algebraic growth period occurred, and then used as a first seed culture solution. The first culture solution was inoculated on 1 L of tryptic soy broth (Difco, USA) and cultured at 35° C. until an algebraic growth period occurred, and then used as a second seed culture solution.

To a 30 L fermenter, 20 L of hyaluronic acid production culture medium containing 60 g/L of glucose, 5 g/L of yeast extract, 17 g/L of casein peptone, 7 g/L of glutamic acid, 0.7 g/L of magnesium sulfate, 2.5 g/L of potassium diphosphate, and 5.0 g/L of sodium chloride was introduced and sterilized, and 1000 ml of the second seed culture solution was inoculated thereon. Culture was conducted at a temperature of 35° C. and a pH of 6.95 to 7.05 for 20 hours.

3-2. Preparation of Culture Filtrate

The hyaluronic acid culture solution was diluted such that the concentration of hyaluronic acid became 0.1 to 0.2%. 0.02% lauryl sulfate and 0.05% formalin solution were added thereto and agitated for 3 hours. Then, bacteria were removed by centrifugation or filtration to prepare a culture filtrate.

3-3. SP207 Resin Treatment

The culture filtrate was titrated such that the pH became 7.5 to 8.5, 3 (w/v) % of aromatic adsorption resin SP207 was added, and exothermic material was adsorbed while agitating at 4 to 10° C. for 3 hours. Then, the adsorption resin-treated solution was filtered to obtain a filtrate from which the adsorption resin was removed, and ultrafiltration was conducted.

3-4. Active Carbon Treatment

To the filtrate, 0.9 (w/v) % of NaCl and 3 (w/v) % of active carbon was added, and it was agitated for 2 hours to adsorb protein and nucleic acid, etc. into the active carbon. Then, filtration was conducted to obtain a hyaluronic acid aqueous solution from which the active carbon was removed.

3-5. Ethanol Precipitation

To the hyaluronic acid aqueous solution, NaCl was added such that its concentration became 1 M, and the solution was filtered using a 0.2 µm filter. Then, ethanol was added in a volume of 1.5 to 3 times that of the solution to precipitate hyaluronic acid and its salt, and it was then washed with 70% ethanol several times. The precipitate was dried under sterilized conditions to obtain hyaluronic acid and its salt.

EXAMPLE 4

Purification of Hyaluronic Acid Using Aromatic Adsorption Resin HP20

Hyaluronic acid and its salt were purified by the same method as in Example 3, except that HP20 was used as an adsorption resin.

EXAMPLE 5

Purification of Hyaluronic Acid Using Aromatic Adsorption Resin SP207 after Active Carbon Treatment Hyaluronic acid and its salt were purified by the same method as in Example 3, except that SP207 was adsorbed after the active carbon treatment.

EXAMPLE 6

Purification of Hyaluronic Acid Using Aromatic Adsorption Resin HP20 after Active Carbon Treatment Hyaluronic acid and its salt were purified by the same method as in Example 4, except that HP20 was adsorbed after the active carbon treatment.

EXAMPLE 7

Purification of Hyaluronic Acid Using SP207

Hyaluronic acid and its salt were purified by the same method as in Example 3, except that *Streptococcus zooepidemicus* (KCTC3318) was used as a hyaluronic acid producing strain.

COMPARATIVE EXAMPLE 2

Hyaluronic acid and its salt were purified by the same method as in Example 3, except that an aromatic resin adsorption step was omitted.

Experiment: Measurement of Hyaluronic Acid Purification Yield

The purities of the hyaluronic acid and its salts purified by the methods of Examples 3 to 7 and Comparative Example were measured.

A. Hyaluronic acid yield: Hyaluronic acid yield was quantified by a modified carbazole method, and initial volume and final volume were compared.

B. Measurement of exothermic material: Hyaluronic acid and its salt were dissolved in water containing exothermic material of 0.001 EU/ml or less such that its density became 1.5 g/L, and then analyzed using LAL (Limulus Amebocyte Lysate) from Charles River Endosafe according to the attached manual. The analyzed value was shown as endotoxin units (EU) existing per 1 mg of hyaluronic acid.

C. Purity test: The purity test was conducted by a carbazole method (Anal. Biochem., 4,330 (1962)).

D. Protein content: The protein content was measured by the Lowry method.

E. Nucleic acid content: Hyaluronic acid and its salt were dissolved in a saline solution to 1%, and then adsorbancy was measured at 260 nm.

The results were described in the following Table 1.

TABLE 1

| | Results | | | | | |
|---|---|---|---|---|---|---|
| Item | Example 3 | Example 4 | Example 5 | Example 6 | Example 7 | Comparative Example 2 |
| Yield | 78% | 80% | 82% | 79% | 78% | 79% |
| Purity(%) | 99.0 | 99.0 | 99.0 | 99.0 | 99.0 | 95 |

TABLE 1-continued

| Item | Results | | | | | |
|---|---|---|---|---|---|---|
| | Example 3 | Example 4 | Example 5 | Example 6 | Example 7 | Comparative Example 2 |
| Exothermic Material (EU/mg) | <0.005 | <0.005 | <0.005 | <0.005 | <0.005 | 0.1 |
| Protein (%) | <0.01% | <0.01% | <0.01% | <0.01% | <0.01% | 0.2 |
| Nucleic acid | ND | ND | ND | ND | ND | 0.1% |
| Molecular weight (million Da) | 5.3 | 5.2 | 5.5 | 5.4 | 2.5 | 5.4 |
| Metal ions | | | | | | |
| Iron(ppm) | <1 ppm | <1 ppm | <1 ppm | <1 ppm | <1 ppm | <1 ppm |
| Lead(ppm) | <1 ppm | <1 ppm | <1 ppm | <1 ppm | <1 ppm | <1 ppm |
| arsenic (ppm) | <1 ppm | <1 ppm | <1 ppm | <1 ppm | <1 ppm | <1 ppm |

As can be seen from Table 1, the hyaluronic acid and its salt purified by Examples 1 to 7 had a high purity of 99%. Meanwhile, the hyaluronic acid purified by Comparative Example had a purity of 95%. In addition, the hyaluronic acid and its salt of Examples 3 to 7 have much lower contents of exothermic material, protein, and nucleic acid than Comparative Example.

What is claimed is:

1. A biologically pure microorganism of *Streptococcus* sp. KL0188 strain KCTC 10248BP, which is a hyaluronic acid producing microorganism strain that does not express hyaluronidase and that shows a non-hemolytic property.

\* \* \* \* \*